| (12) | United States Patent | (10) Patent No.: | US 8,916,623 B2 |
|---|---|---|---|
| | Riedel et al. | (45) Date of Patent: | Dec. 23, 2014 |

(54) SURFACTANT-CONTAINING COMPOSITION FOR DENTAL IMPRESSION

(75) Inventors: Norman Hendrik Riedel, Frankfurt am Main (DE); Manfred Thomas Plaumann, Cuxhaven (DE)

(73) Assignee: Voco GmbH, Cuxhaven (DE)

( * ) Notice: Subject to any disclaimer, the term of this patent is extended or adjusted under 35 U.S.C. 154(b) by 658 days.

(21) Appl. No.: 13/105,619

(22) Filed: May 11, 2011

(65) Prior Publication Data

US 2011/0281237 A1 Nov. 17, 2011

(30) Foreign Application Priority Data

May 12, 2010 (DE) .......................... 10 2010 028 973

(51) Int. Cl.
 *A61K 6/10* (2006.01)
 *A61C 9/00* (2006.01)

(52) U.S. Cl.
 CPC .................................. *A61K 6/10* (2013.01)
 USPC .............. 523/109; 433/214; 264/16; 106/35

(58) Field of Classification Search
 USPC ............... 523/109; 433/214; 264/16; 106/35
 See application file for complete search history.

(56) References Cited

U.S. PATENT DOCUMENTS

| 4,657,959 A | 4/1987 | Bryan et al. |
| 5,064,891 A | 11/1991 | Fujiki et al. |
| 5,569,691 A | 10/1996 | Guggenberger et al. |
| 5,750,589 A | 5/1998 | Zech et al. |
| 5,907,002 A | 5/1999 | Kamohara et al. |
| 6,291,546 B1 | 9/2001 | Kamohara et al. |
| 7,812,065 B2 | 10/2010 | Bublewitz et al. |
| 2008/0319100 A1* | 12/2008 | Bublewitz et al. ............ 523/109 |
| 2010/0292362 A1 | 11/2010 | Zech et al. |

FOREIGN PATENT DOCUMENTS

| DE | 102009021553 A1 | 11/2010 |
| EP | 0231420 A1 | 8/1987 |
| EP | 1290998 A1 | 3/2003 |
| WO | 2004058196 A | 7/2004 |

* cited by examiner

*Primary Examiner* — Michael Pepitone
(74) *Attorney, Agent, or Firm* — Duane Morris LLP; J. Rodman Steele, Jr.; Gregory M. Lefkowitz

(57) ABSTRACT

A composition for obtaining dental impressions and methods of using and making the same are disclosed. The compositions can include curable base compositions and surfactant systems. The surfactant system can include (i) 0.5 to 3 wt-% of a first surfactant comprising end-capped polyoxyethylene alkyl ether, end-capped polyoxypropylene alkyl ether, end-capped polyoxyethylene-polyoxypropylene alkyl ether or mixtures thereof, (ii) 0.5 to 3 wt-% of a second surfactant, selected from the group of non-ionic fluorosurfactants, (iii) 0 to 3 wt-% of a third surfactant, selected from the group of silicone surfactants, wherein the total quantity of first, second and third surfactant is from 1.5 to 6 wt-%. The mass ratio of the first surfactant to the second surfactant can be 1.4 or less when the content of the third surfactant is less than 0.5 wt-% and the total quantity of first and second surfactant is 2 wt-% or less.

18 Claims, No Drawings

SURFACTANT-CONTAINING COMPOSITION FOR DENTAL IMPRESSION

CROSS-REFERENCE TO RELATED APPLICATIONS

This application claims priority of German Patent Application No 10 2010 028 973.6, filed May 12, 2010, the entire contents of which are incorporated herein by reference.

FIELD OF THE INVENTION

The present invention relates to a curable, single- or multi-component composition for dental impression (hereafter also called dental impression materials) comprising
  a curable base composition
and
  a surfactant system comprising or consisting of
    0.5 to 3% by weight of a first surfactant, selected from the group consisting of end-capped polyoxyethylene alkyl ether, end-capped polyoxypropylene alkyl ether, end-capped polyoxyethylene polyoxypropylene alkyl ether and mixtures thereof,
    0.5 to 3% by weight of a second surfactant, selected from the group of non-ionic fluorosurfactants,
    0 to 3% by weight of a third surfactant, selected from the group of silicone surfactants,
    wherein the total quantity of first, second and third surfactant is within the range of from 1.5% by weight to 6% by weight,
  provided that
    the mass ratio of the first surfactant to the second surfactant is 1.4 or less when the content of the third surfactant is within the range of from 0 to less than 0.5% by weight and the total quantity of first and second surfactant is 2% by weight or less,
all the percentages by weight being based on the total mass of the composition.

The invention also relates to the use of a composition according to the invention as a dental impression system and to a process for the preparation of a composition according to the invention.

BACKGROUND

The wetting behavior of a dental impression material relative to saliva is one of the critical parameters in respect of the accuracy of the dental impression which is obtained. Conventional impression materials, for example impression materials based on polydimethylsiloxane have, however, an inadequate wetting behavior relative to aqueous media, so that in some cases, contact angles of 90° and more result. Therefore, in order to optimize the surface affinity of dental impression materials in a hydrophilic environment, surfactant additives have been proposed and used for many years.

U.S. Pat. No. 4,657,959 discloses curable silicone compositions which contain a surfactant, in particular a fluorosurfactant as dental impression materials. If a drop of water is dripped onto the surface of such an impression material, according to the US document a contact angle of less than 10° is obtained after three minutes.

EP 1 290 998 B1 discloses a composition for dental impression based on addition-crosslinking organopolysiloxanes, where the composition contains a non-ionic surfactant and/or a polyether-modified silicone oil.

WO 2004/058 196 A1 discloses a dental impression material based on polyvinylsiloxane, in which by using a non-ionic surfactant, in particular PEG8 Methicone, a contact angle of less than 10° is to be achieved within 15 seconds, 15 minutes after curing. However, such a wetting behavior is only relevant for the surface affinity in the case of a plaster cast, but not for taking impressions in a patient's mouth.

EP 0 729 341 B1 relates to a dental impression material which contains polyethercarbosilanes for hydrophilization. In this case, contact angles of only 42° or more are achieved.

EP 0 231 420 B1 describes the hydrophilization of a dental impression material based on addition-crosslinking silicones by silicone polyether.

Furthermore, U.S. Pat. No. 5,064,891 A discloses a dental impression material containing a surfactant.

U.S. Pat. No. 5,907,002 A describes dental impression compositions which contain a non-ionic surfactant. Polyoxyethylene alkyl ether, polyoxypropylene alkyl ether, polyoxyethylene alkyl phenylether and various fatty acid esters and fluoroalkylethylene oxide surfactants are given as examples of non-ionic surfactants.

DE 199 22 929 A1 and the corresponding U.S. Pat. No. 6,291,546 B1 describes compositions containing one or more non-ionic surfactants for taking dental impressions of the oral mucosa. Polyoxyethylene alkyl ether, polyoxypropylene alkyl ether, polyoxyethylene alkyl phenylether, in particular polyoxyethylene nonylphenyl ether and various fatty acid esters and fluoroalkylethylene oxide surfactants are given as examples of non-ionic surfactants. Compositions comprising any of said ethers as well as a fluorosurfactant are not disclosed.

DE 10 2006 001 126 A1 describes compositions for dental impression materials which, in addition to a curable polymer, also contain at least one non-ionic surfactant with a molar mass of less than 6000 g/mol which has a (poly)alkylene oxide radical and a silicon-containing group (hereafter called a silicon-containing surfactant) and at least one non-ionic fluorosurfactant which has a (poly)alkylene oxide radical and at least one partially or perfluorinated hydrocarbon radical which is connected to the (poly)alkylene oxide radical via an oxygen atom or an ester group (hereafter called a fluorosurfactant). The weight ratio of silicon-containing surfactant to fluorosurfactant is within the range of from 100:1 to 1:100, preferably 50:1 to 1:50, more preferably 10:1 to 1:10 and particularly preferably 5:1 to 1:5. In preferred compositions, the content of silicon-containing surfactant and fluorosurfactant, based on the total mass of the composition, is in each case 0.001 to 10% by weight. In addition to the silicon-containing surfactant described above and the fluorosurfactant described above, the composition can contain further surfactants, inter alia alkyl-, aryl-, aralkyl-capped non-ionic surfactants, preferably alkyl-capped fatty alcohol ethoxylates, silicone surfactants, polyethercarbosilanes, carbosilane surfactants and fluorosurfactants which are alkyl-capped and in particular alkyl-capped fatty alcohol ethoxylates.

The dental impression materials which can be obtained from the compositions disclosed in patent application DE 10 2006 001 126 A1 are said to have an initial contact angle (measured between 3 and 10 seconds drop age, the drop of water being delivered 40 seconds after the start of the mixing of the catalyst and base components of the curable polymer system) of <10°, and during the processing time of between 0 and 3 minutes have an equilibrium contact angle of <10°. In comparative examples, compositions were also tested which contained a fluorosurfactant (0.75 or 1.5% by weight, based on the total mass of the composition) and a non-ionic alkyl-capped fatty alcohol ethoxylate surfactant with a surface tension of 29 mN/m (0.2% by weight, based on the total weight of the composition), but no silicon-containing surfactant.

However, it is stated that the thus obtained impression materials are insufficiently hydrophilic, i.e. within a period of 30 seconds after delivery of a drop of water, a contact angle was obtained which was significantly greater than 10°. Compositions containing 0.2% by weight of a non-ionic alkyl-capped fatty alcohol ethoxylate surfactant are said to have only produced impression materials with an acceptable wetting behavior when the composition also contained 0.75% by weight of fluorosurfactant and 0.75% of silicon-containing surfactant or 0.375% by weight of fluorosurfactant and 1.125% by weight of silicon-containing surfactant.

DE 10 2009 021 553 A1 discloses a curable composition comprising curable polymers and also at least one non-ionic or ionic fluorosurfactant selected from a group consisting of eight specific classes of fluorosurfactants, Additionally, the composition may comprise at least one additional fluorosurfactant and/or at least one silicon-containing surfactant having a molar mass of less than 6000 g/mol and/or a polyether containing alkylene residues and/or alkinyl residues and/or a polyether which is hydroxyl and/or aryloxy and/or arylalkyloxy and/or alkoxy-terminated. An upper limit of the surfactant content of the curable composition is not disclosed.

DE 43 06 997 A1 discloses a rubber-elastic composition, for instance a dental impression composition based on vulcanizable polyether materials wherein the composition comprises at least one hydrophilic silicone oil and/or at least one non-ionic surfactant. Regarding the non-ionic surfactant, numerous alternatives from the most different classes of surfactants are proposed, among others fluorinated hydrocarbon compounds as well as alkoxylated fatty alcohols and acylated alkoxylated fatty alcohols. Compositions comprising an alkoxylated fatty alcohol as well as a fluorosurfactant are not disclosed. Any composition described by way of example contains only one single surfactant. In the completely vulcanized and completely polymerized state, the rubber-elastic compositions shall have a 10 second wetting angle of less than 55°, preferably less that 45° and especially less than 35°. The wetting angle of the completely polymerized composition does not allow for any conclusion how well the impression composition wets and flows onto the moist dental substance and oral mucosa which are covered with saliva and possibly blood, when dental impressions are taken, i.e. in the not yet cured state of the impression composition.

WO 2009/079534 A2 discloses a curable dental composition comprising one or more surfactants and a fluorine-containing compound of the formula given there. The surfactant may be for instance a silicon-containing surfactant or an ethoxylated fatty alcohol. Thereby, it was found that dental compositions containing a fluoro-compound as defined in WO 2009/079534 A2 and no surfactant do not show an improved wetting behavior compared to compositions containing a typical fluorosurfactant as, e.g., Zonyl™ FSO-100, while on the other hand dental compositions comprising a fluoro-compound as defined in WO 2009/079534 A2 in combination with a surfactant show an improved wetting behavior.

In dental technology, there is always a need for compositions for dental impression materials which are sufficiently hydrophilic so that when dental impressions are taken, i.e. in the not yet cured state of the impression material, the moist dental substance and oral mucosa which are covered with saliva and possibly blood can be immediately, preferably spontaneously, wetted and the dental impression material can flow directly thereonto so that an impression, accurate in every detail, of the dental situation is obtained.

SUMMARY OF THE INVENTION

The object of the present invention was to provide a suitable composition of this type for dental impression.

The object is achieved according to the invention by a curable, single or multi-component composition for dental impression, comprising
    a curable base composition
and
    a surfactant system, comprising or consisting of
        0.5 to 3% by weight of a first surfactant, selected from the group consisting of end-capped polyoxyethylene alkyl ether, end-capped polyoxypropylene alkyl ether, end-capped polyoxyethylene polyoxypropylene alkyl ether and mixtures thereof,
        0.5 to 3% by weight of a second surfactant, selected from the group of non-ionic fluorosurfactants,
        0 to 3% by weight (i.e. 0% by weight or a quantity of up to 3% by weight) of a third surfactant, selected from the group of silicone surfactants,
        wherein the total quantity of first, second and third surfactant is within the range of from 1.5% by weight to 6% by weight,
    provided that
        the mass ratio of the first surfactant to the second surfactant is 1.4 or less when the content of the third surfactant is within the range of from 0 to less than 0.5% by weight and the total quantity of first and second surfactant is 2% by weight or less,
all the percentages by weight being based on the total mass of the composition.

A curable composition of the type described above is preferably used which comprises
    a curable base composition
and
    a surfactant system comprising
        a first surfactant selected from the group consisting of end-capped polyoxyethylene alkyl ether, end-capped polyoxypropylene alkyl ether, end-capped polyoxyethylene polyoxypropylene alkyl ether and mixtures thereof,
        a second surfactant selected from the group of non-ionic fluorosurfactants,
        optionally a third surfactant selected from the group of silicone surfactants,
    provided that the surfactant system contains
        0.75 to 3% by weight of the second surfactant,
        0 to less than 0.5% by weight of the third surfactant,
    or the surfactant system contains
        0.5 to 2.5% by weight of the first surfactant,
        0.5 to 2.5% by weight, preferably 0.75 to 2.5% by weight of the second surfactant
        0.5 to 2.5% by weight of the third surfactant.

It has surprisingly been found in our own experiments that a composition according to the invention has the desired wetting behavior on curing. During curing, a particularly preferred composition according to the invention has a particular wetting behavior such that when a drop of water is applied to the surface of the curing impression material 40 seconds after the start of curing, a contact angle of 10° is achieved within a short time, i.e. within 30 seconds or less, preferably within 10 seconds or less.

DETAILED DESCRIPTION

Where there is a total content of first, second and third surfactant of less than 1.5% by weight, hydrophilization is inadequate, i.e. when a drop of water is applied to the curing impression material, a contact angle of less than 10° is never obtained or at least is not obtained after a short time.

A total content of first, second and third surfactant of more than 6% by weight adversely affects the binding behavior of the curable base system; the system then cures very slowly and eventually in an incomplete manner. The reason for this, inter alia, is the increasing complexing of the catalyst by the surfactants.

The first surfactant to be used according to the invention is selected from the group consisting of end-capped polyoxyethylene alkyl ether, end-capped polyoxypropylene alkyl ether, end-capped polyoxyethylene polyoxypropylene alkyl ether and mixtures thereof. "End-capped" as used herein means that in the terminal hydroxyl groups, the hydrogen atoms are substituted by alkyl groups. Preferably, in the terminal hydroxyl groups, the hydrogen atoms are substituted by alkyl groups comprising one to six carbon atoms, more preferably by alkyl groups comprising one to three carbon atoms. Also particularly preferred are end-capped polyoxyethylene alkyl ethers, end-capped polyoxypropylene alkyl ethers, end-capped polyoxyethylene polyoxypropylene alkyl ethers, wherein a first terminal hydroxy group is substituted by an alkyl group having 6 to 23 carbon atoms and a second terminal hydroxy group is substituted by an alkyl group having 1 to 6, preferably 1 to 3 carbon atoms, and mixtures thereof.

Accordingly, preferably the first surfactant is preferably a compound of the formula

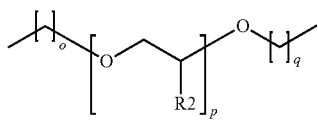

wherein
o is an integer from 5 to 22
p is an integer from 2 to 20
q is an integer from 0 to 5.
R2 is hydrogen or a methyl group wherein within a molecule R2 can have different meanings within the scope of the given definition.

Thus, the first surfactants to be used according to the invention do not contain any free terminal hydroxyl groups.

In a preferred variant, the first surfactant comprises end-capped polyoxypropylene alkyl ethers and/or end-capped polyoxyethylene polyoxypropylene alkyl ethers preferably in admixture with end-capped polyoxyethylene alkylether.

Preferably, the first surfactant is an end-capped fatty alcohol ethoxylate. Fatty alcohol ethoxylates are in particular non-ionic surfactants which are obtained by reaction of a fatty alcohol (primary alcohol having 6 to 22 carbon atoms) with ethylene oxide in the presence of basic or acid catalysts at temperatures from 120 to 200° C. and pressures from 1 to 10 bar.

A first surfactant which is preferably used is an end-capped fatty alcohol ethoxylate with a surface tension of 30 mN/m (in deionized water at 20° C. and in a concentration of 1 g/l) and a turbidity titration number according to DIN 53989 of approximately 7.

A further first surfactant which is preferably used is an end-capped fatty alcohol ethoxylate with a surface tension of 29 mN/m (in deionized water at 20° C. and in a concentration of 1 g/l) and a turbidity titration number according to DIN 53989 of approximately 22.

A further first surfactant which is preferably used is an end-capped fatty alcohol ethoxylate with a surface tension of 29 mN/m (in deionized water at 20° C. and in a concentration of 1 g/l) and a turbidity titration number according to DIN 53989 of approximately 15.

The second surfactant to be used according to the invention is selected from the group of non-ionic fluorosurfactants. The non-ionic fluorosurfactant is preferably a compound of formula:

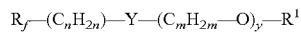

wherein $R_f$ is a radical of the formula $C_xF_{2x+1}$,
x is an integer from 1 to 30, preferably 2 to 18,
n is an integer from 0 to 30, preferably 1 to 3,
Y is —O— or —CO—O—, preferably —O—,
m is an integer from 2 to 6, preferably 2 or 3, more preferably 2,
y is an integer from 1 to 60, preferably 1 to 25 and
$R^1$ represents hydrogen or a monovalent organic radical, preferably hydrogen, $C_1$-$C_6$ alkyl or phenyl, more preferably hydrogen or an alkyl radical,
where m can assume different values within a molecule in the scope of the given definition.

More preferably, the non-ionic fluorosurfactant is a compound of formula:

or

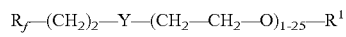

wherein $R_f$ is as defined above and is preferably a radical of formula:
$C_xF_{2X+1}$ where x=1 to 18, in particular x=4 to 12,
Y is —O—,
$R^b$ is $C_1$-$C_6$ alkyl, preferably methyl or ethyl, and
$R_1$ is as defined above and is preferably hydrogen, $C_1$-$C_6$ alkyl, in particular methyl, $C_1$-$C_6$ alkenyl, preferably vinyl, or phenyl.

More preferably, the fluorosurfactant is a compound of formula:

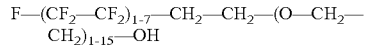

or

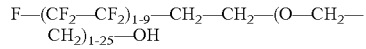

A second surfactant which is more preferably used according to the invention is an ethoxylated non-ionic fluorosurfactant with a surface tension of 19 mN/m (in deionized water at 25° C. and in a concentration of 0.1 g/l).

In a composition according to the invention which contains a surfactant system comprising a first, second and third surfactant, the third surfactant is selected from the group of silicone surfactants. Silicone surfactants are surfactants, the molecules of which have at least one group containing a silicon atom. Non-ionic silicone surfactants are preferred, in particular those non-ionic silicone surfactants which have at least one (poly)alkylene oxide radical. Particularly preferred are non-ionic surfactants with a molar mass of less than 6000 g/mol which have at least one (poly)alkylene oxide radical as well as a silicon-containing group.

A third surfactant which is more preferably used according to the invention is polyalkylene oxide-modified polydimethylsiloxane with a surface tension of 20.5 mN/m (in deionized water at 25° C. and in a concentration of 1 g/l).

The composition according to the invention is preferably in the form of one or more pastes.

The composition according to the invention can be present as a single component or multi-component system, depending on the choice of the curable base composition. In the case of a single component system, all the constituents of the composition according to the invention are present next to one another in a mixture. In the case of a multi-component system, the constituents of the composition according to the invention are present in components which are separated from one another and are only mixed together just before use. If the composition is a multi-component, preferably two-component system comprising a first component and a second component, the constituents thereof are adapted to one another such that curing is initiated by mixing the first and second components as well as optionally present further components.

If the composition according to the invention is a two or multi-component system, the two or more components are preferably in the form of pastes.

The curable base composition of the composition according to the invention is preferably a curable polymer system. The curable base composition of the composition according to the invention is preferably selected from the group of
organopolysiloxanes crosslinking by an addition reaction,
organopolysiloxanes crosslinking by a condensation reaction,
polyethers containing aziridino radicals crosslinking by an addition reaction,
polyethers containing alkenyl radicals crosslinking by an addition reaction,
and
polyethers containing alkoxysilyl radicals crosslinking by a condensation reaction.

The curable base composition of the composition according to the invention is preferably selected from the group of organopolysiloxanes crosslinking by an addition reaction.

A composition according to the invention (preferably a two or multi-component system) is preferred which comprises a curable base composition containing an organopolysiloxane crosslinking by an addition reaction, comprising
an organopolysiloxane with at least two ethylenically unsaturated groups
and
an organohydrogen polysiloxane.

More preferably, the curable base composition contained in the composition according to the invention is an organopolysiloxane crosslinking by an addition reaction, comprising
an organopolysiloxane with at least two ethylenically unsaturated groups
and
an organohydrogen polysiloxane.

This curable composition according to the invention is preferably a two or multi-component system wherein
a first component comprises organopolysiloxane with at least two ethylenically unsaturated groups and the organohydrogen polysiloxane,
and
a second component comprises a catalyst, in particular a hydrosilylation catalyst,
wherein the first surfactant and the second surfactant (as well as optionally further surfactants) are preferably contained in the first and/or second component.

Furthermore, a curable composition according to the invention is preferred which comprises a plurality of components, preferably two components, in particular
a first component comprising the organohydrogen polysiloxane and optionally organopolysiloxane with at least two ethylenically unsaturated groups
and
a second component comprising organopolysiloxane with at least two ethylenically unsaturated groups and a hydrosilylation catalyst
wherein the first surfactant and the second surfactant (as well as optionally further surfactants) are preferably contained in the first and/or second component.

Organopolysiloxanes are preferred with at least two ethylenically unsaturated groups selected from the group consisting of
vinylpolydimethylsiloxane with a viscosity of approximately 1000 mPas at 20° C.
vinylpolydimethylsiloxane with a viscosity of approximately 65000 mPas at 20° C.

The organohydrogen polysiloxanes are preferably selected from the group consisting of
Dihydrogenpolydimethylsiloxane with an SiH content of approximately 3.6 mmol/kg
Polyhydrogenmethylsiloxane with an SiH content of approximately 2.1 mmol/kg
Polyhydrogenmethylsiloxane with an SiH content of approximately 2.3 mmol/kg
Polyhydrogenmethylsiloxane with an SiH content of approximately 2.6 mmol/kg
Polyhydrogenmethylsiloxane with an SiH content of approximately 3.0 mmol/kg
Polyhydrogenmethylsiloxane with an SiH content of approximately 4.3 mmol/kg
Polyhydrogenmethylsiloxane with an SiH content of approximately 7.3 mmol/kg
Polyhydrogenmethylsiloxane with an SiH content of approximately 7.8 mmol/kg
Polyhydrogenmethylsiloxane with an SiH content of approximately 15 mmol/kg The composition according to the invention can also comprise one or more fillers and optionally further additives. These are known per se by a person skilled in the art. For example, the composition according to the invention can contain initiators or catalysts which respectively initiate and accelerate curing. Platinum-containing catalysts are typically used.

Preferred fillers are selected from the group consisting of aluminum hydroxide, zinc oxide, titanium dioxide, zirconium oxide, silicon dioxide (for example in the form of silica flour or precipitated and/or pyrogenic silica). The particle surfaces of these fillers are preferably modified with organic radicals.

A composition according to the invention is particularly preferred which comprises
a curable base composition and
a surfactant system comprising or consisting of
0.75 to 3% by weight of a first surfactant selected from the group consisting of end-capped polyoxyethylene alkyl ether, end-capped polyoxypropylene alkyl ether, end-capped polyoxyethylene polyoxypropylene alkyl ether and mixtures thereof,
0.75 to 3% by weight of a second surfactant, selected from the group of non-ionic fluorosurfactants,
0 to less than 0.5% by weight of a third surfactant, selected from the group of silicone surfactants,
wherein the total quantity of first, second and third surfactant is within the range of from 2 to 6% by weight,
the mass ratio of the first surfactant to the second surfactant is 1.4 or less when the content of the third surfactant is within the range of from 0 to less than 0.5% by weight and the total quantity of first and second surfactants is 2% by weight, all the percentages by weight being based on the total mass of the composition.

A composition according to the invention is also preferred which comprises
- a curable base composition and
- a surfactant system comprising or consisting of
    - 0.5 to 2.5% by weight of a first surfactant selected from the group consisting of end-capped polyoxyethylene alkyl ether, end-capped polyoxypropylene alkyl ether, end-capped polyoxyethylene polyoxypropylene alkyl ether and mixtures thereof,
    - 0.5 to 2.5% by weight of a second surfactant, selected from the group of non-ionic fluorosurfactants,
    - 0.5 to 2.5% by weight of a third surfactant, selected from the group of silicone surfactants,
  - wherein the total quantity of first, second and third surfactant is within the range of from 1.75% by weight to 6% by weight,
  - and, when the total quantity of first, second and third surfactant amounts to 2% by weight or less, the quantity of the second surfactant amounts to at least 0.75% by weight,
  - all the percentages by weight being based on the total mass of the composition.

The preferred compositions according to the invention described above make it possible to produce impression materials which, during the taking of dental impressions, i.e. in the not yet cured state of the impression material, almost spontaneously wet the moist dental substance and oral mucosa covered with saliva and possibly blood and flow directly onto them. This can be demonstrated in an impressive manner in experiments using two or multi-component systems, for example, in that a drop of water which is applied to the surface of the curing impression material 40 seconds after the start of the mixing of the components of the two or multi-component curable base system achieves a contact angle of 10° within less than 10 seconds. Almost spontaneously (initially), a drop of water spreads over the impression materials which can be produced from these preferred compositions according to the invention.

As described above, the invention also comprises a curable composition with a surfactant system which, in addition to a first surfactant, as described above, and a second surfactant, as described above, comprises as third surfactant a surfactant selected from the group of silicone surfactants. However, for some purposes, it is preferable for the composition according to the invention to be free from non-ionic surfactants with a molar mass of less than 6000 g/mol, specifically less than 4000 g/mol and in particular from 350 to 2000 g/mol which have at least one (poly)alkylene oxide radical and a silicon-containing group. In particular, the composition according to the invention is preferably free from
- the organosiloxane surfactants of formula II and/or formula III disclosed in the above-mentioned patent application DE 10 2006 001 126 A1, and
- the organocarbonsilane surfactants of formulae IV, V and VI disclosed in the above-mentioned patent application DE 10 2006 001 126 A1, and
- the non-ionic surfactants of formulae VII, VIII, IX and X having silicon and at least one (poly)alkylene oxide radical, disclosed in the above-mentioned patent application DE 10 2006 001 126 A1.

Also preferred is a composition according to the invention which is free from:
- the organosiloxane surfactants of formula II and formula III disclosed in the above-mentioned patent application DE 10 2009 021 553 A1, and the organocarbonsilane surfactants of formulae IV, V and VI disclosed in the above-mentioned patent application DE 10 2009 021 553 A1, and the non-ionic surfactants of formulae VII, VIII, IX and X having silicon and at least one (poly)alkylene oxide radical disclosed in the above-mentioned patent application DE 10 2009 021 553 A1 and/or
- the fluorosurfactants a) through h) disclosed in the above-mentioned patent application DE 10 2009 021 553 A1.

Particularly preferred is a composition according to the invention which is free from non-ionic surfactants which have at least one (poly)alkylene oxide radical and a silicon-containing group. A composition according to the invention which is most particularly preferred is free overall from silicon-containing surfactants.

Also preferred is a composition according to the invention which is free from
- the fluorine-containing compounds defined in claims 1 to 11 of the above-mentioned patent application WO 2009/079534 A2 and/or
- the surfactants defined in claim 12 of the above-mentioned patent application WO 2009/079534 A2 and/or
- polyethylene glycol dimethyl ether.

More preferred is a composition according to the invention which is free from
(i) the organosiloxane surfactants of formula II and/or formula III disclosed in the above-mentioned patent application DE 10 2006 001 126 A1, and
   the organocarbonsilane surfactants of formulae IV, V and VI disclosed in the above-mentioned patent application DE 10 2006 001 126 A1, and
   the non-ionic surfactants of formulae VII, VIII, IX and X having silicon and at least one (poly)alkylene oxide radical, disclosed in the above-mentioned patent application DE 10 2006 001 126 A1;
and
(ii) the organosiloxane surfactants of formula II and formula III disclosed in the above-mentioned patent application DE 10 2009 021 553 A1, and the organocarbonsilane surfactants of formulae IV, V and VI disclosed in the above-mentioned patent application DE 10 2009 021 553 A1, and the non-ionic surfactants of formulae VII, VIII, IX and X having silicon and at least one (poly)alkylene oxide radical disclosed in the above-mentioned patent application DE 10 2009 021 553 A1 and/or
   the fluorosurfactants a) through h) disclosed in the above-mentioned patent application DE 10 2009 021 553 A1.
and
(iii) the fluorine-containing compounds defined in claims 1 to 11 of the above-mentioned patent application WO 2009/079534 A2 and/or
   the surfactants defined in claim 12 of the above-mentioned patent application WO 2009/079534 A2 and/or
   polyethylene glycol dimethyl ether.

Most preferred is a composition according to the invention which is free from all compounds for which it is mentioned above that a composition according to the invention is preferably free from said compound.

The invention also relates to the use of a composition according to the invention as a dental impression system. The term "dental impression system" is understood as meaning a single or multi-component composition which, in the case of a multi-component composition, is used immediately after the components have been mixed together and cures while being mixed, to produce a dental impression of a patient.

Use of the dental impression system includes a method of obtaining a dental impression that includes (i) producing a curable composition as set forth herein; and contacting the curable composition with a dental feature to form an impression of the dental feature. The method can also include curing the curable composition containing the impression of the dental feature.

The present invention also relates to a process for the preparation of a composition according to the invention, comprising the steps:

preparation of a curable base composition
preparation of a surfactant system comprising or consisting of
0.5 to 3% by weight of a first surfactant, selected from the group polyoxypropylene alkyl ether, end-capped polyoxyethylene polyoxypropylene alkyl ether and mixtures thereof,
0.5 to 3% by weight of a second surfactant, selected from the group of non-ionic fluorosurfactants,
0 to 3% by weight of a third surfactant, selected from the group of silicone surfactants,
wherein the total quantity of first, second and third surfactant is within the range of from 1.5% by weight to 6% by weight,
provided that
the mass ratio of the first surfactant to the second surfactant is 1.4 or less when the content of the third surfactant is within the range of from 0 to less than 0.5% by weight and the total quantity of first and second surfactant is 2% by weight or less,
all the percentages by weight being based on the total mass of the composition.

A composition prepared by the process according to the invention is preferably a multi-component, preferably two-component system comprising a first component and a second component, the constituents of which are adapted to one another such that curing is initiated by mixing the first and second components as well as optionally present further components, the first surfactant and the second surfactant (and optionally further surfactants) preferably being contained in the first and/or second component.

In the following, the invention will be described in more detail on the basis of examples.

Exemplary Embodiments

All the exemplary embodiments relate to two-component compositions with a curable base composition selected from the group of organopolysiloxanes crosslinking by an addition reaction. The composition comprises components I and II. Component I comprises the base mass of the curable base composition and contains organohydrogen polysiloxanes (siloxanes 3 and 4, see below) and an organopolysiloxane with at least two ethylenically unsaturated groups (siloxane 1) and optionally one or more surfactants. Component II comprises the catalyst component of the curable base composition and contains organopolysiloxanes with at least two ethylenically unsaturated groups (siloxanes 1 and 2, see below), a hydrosilylation catalyst and optionally one or more surfactants.

The following substances were used for the preparation of components I and II:

Siloxane 1 Vinylpolydimethylsiloxane with a viscosity of approximately 1000 mPas at 20° C.
Siloxane 2 Vinylpolydimethylsiloxane with a viscosity of approximately 65000 mPas at 20° C.
Siloxane 3 Dihydrogenpolydimethylsiloxane with an SiH content of approximately 3.6 mmol/kg
Siloxane 4 Polyhydrogenmethylsiloxane with an SiH content of approximately 2.3 mmol/kg
Silica flour 1 Hydrophobized silica flour with an average grain size of 3 μm
Catalyst 1 Platinum catalyst with a platinum content of 1% by weight
Surfactant 1 End-capped fatty alcohol ethoxylate with a surface tension of 30 mN/m (in deionized water at 20° C. and in a concentration of 1 g/l)
Surfactant 2 Ethoxylated non-ionic fluorosurfactant with a surface tension of 19 mN/m (in deionized water at 25° C. and in a concentration of 0.1 g/l)
Surfactant 3 Polyalkyleneoxide-modified polydimethylsiloxane with a surface tension of 20.5 mN/m (in deionized water at 25° C. and in a concentration of 1 g/l)

The following variants of component I were prepared for the exemplary embodiments:

Component I: Basic Formulation (without Surfactants)
In a tumbling mixer, 41 parts of a siloxane 1, 12 parts of a siloxane 4, 2 parts of a siloxane 3 and 45 parts of a silica flour 1 were mixed homogeneously. The mixture was then degassed under vacuum for 20 minutes.

Component I: Variant 1
99.5 parts of the basic formulation were mixed homogeneously with 0.5 parts of surfactant 1 in a tumbling mixer and degassed under vacuum for 20 minutes.

Component I: Variant 2
99 parts of the basic formulation were mixed homogeneously with 1 part of surfactant 1 in a tumbling mixer and degassed under vacuum for 20 minutes.

Component I: Variant 3
98 parts of the basic formulation were mixed homogeneously with 2 parts of surfactant 1 in a tumbling mixer and degassed under vacuum for 20 minutes.

Component I: Variant 4
99 parts of the basic formulation were mixed homogeneously with 1 part of surfactant 3 in a tumbling mixer and degassed under vacuum for 20 minutes.

Component I: Variant 5
98 parts of the basic formulation were mixed homogeneously with 2 parts of surfactant 3 in a tumbling mixer and degassed under vacuum for 20 minutes.

Component I: Variant 6
98 parts of the basic formulation were mixed homogeneously with 1 part of surfactant 1 and with 1 part of surfactant 2 in a tumbling mixer and degassed under vacuum for 20 minutes.

Component I: Variant 7
97.5 parts of the basic formulation were mixed homogeneously with 1 part of surfactant 1 and with 1.5 parts of surfactant 2 in a tumbling mixer and degassed under vacuum for 20 minutes.

Component I: Variant 8
96.5 parts of the basic formulation were mixed homogeneously with 1 part of surfactant 1 and with 2.5 parts of surfactant 2 in a tumbling mixer and degassed under vacuum for 20 minutes.

The following variants of component II were prepared for the exemplary embodiments:

Component II: Variant A
43 parts of a siloxane 1, 11 parts of a siloxane 2, 45 parts of a silica flour 1 and 1 part of a catalyst 1 were mixed homogeneously in a tumbling mixer. The mixture was then degassed under vacuum for 20 minutes.

Component II: Variant B 99.5 parts of the basic formulation of component II according to variant A were mixed homogeneously with 0.5 parts of surfactant 1 in a tumbling mixer and degassed under vacuum for 20 minutes.

Component II: Variant C 99 parts of the basic formulation of component II according to variant A were mixed homogeneously with 1 part of surfactant 1 in a tumbling mixer and degassed under vacuum for 20 minutes.

Component II: Variant D 98 parts of the basic formulation of component II according to variant A were mixed homogeneously with 2 parts of surfactant 1 in a tumbling mixer and degassed under vacuum for 20 minutes.

Component II: Variant E 99 parts of the basic formulation of component II according to variant A were mixed homogeneously with 1 part of surfactant 3 in a tumbling mixer and degassed under vacuum for 20 minutes.

Component II: Variant F 98 parts of the basic formulation of component II according to variant A were mixed homogeneously with 2 parts of surfactant 3 in a tumbling mixer and degassed under vacuum for 20 minutes.

Component II: Variant G 95 parts of the basic formulation of component II according to variant A were mixed homogeneously with 5 parts of surfactant 3 in a tumbling mixer and degassed under vacuum for 20 minutes.

The compositions described in the following examples according to the invention and in the comparative examples not according to the invention were prepared by combining the different variants of components I and II. The nomenclature of the examples and comparative examples reflects which variant (A-G) of component II was combined with which variant of component I (1-7). Thus, a combination of variant A of component II with variant I of component I forms example A1.

The impression materials were prepared and tested in accordance with ISO 4823.

To determine the contact angle, dynamic contact angle measurements were made using the contact angle measuring device DSA 100 (manufactured by Krüss, Hamburg) which was fitted with a fully automatic measuring system and a temperature chamber for the samples. 40 seconds after the start of mixing of components I and II, a drop of water, 5 µl in volume was applied to the surface of the curing material. The contact angle was determined dynamically for 200 seconds by the "circle fit" method.

The contact angles obtained after 30 seconds are stated in Table 1. A contact angle of 10° was obtained with all the examples according to the invention. The dental impression materials which are produced during curing of these compositions are thus sufficiently hydrophilic in order to flow rapidly onto the moist dental substance and oral mucosa, covered with saliva and possibly blood so that that an impression, accurate in every detail, of the dental situation is obtained.

Table 2 shows the times within which the contact angle of 10° is obtained for the examples according to the invention. Compositions for which the contact angle of 10° is obtained within less than 10 seconds are preferred according to the invention.

Compositions According to the Invention Comprising Surfactant 1 and Surfactant 2

Example A8

50 parts of the paste of component II according to variant A were charged with 50 parts of the paste of component I according to variant 8 into a cartridge (manufactured by Mixpac) and expressed as a homogeneous mixture via a static mixer.

A low-viscosity impression material according to ISO 4823 was obtained, on which an applied drop of water achieved a contact angle of less than 10° after 21 seconds.

Example B7

50 parts of the paste of component II according to variant B were charged with 50 parts of the paste of component I according to variant 7 into a cartridge (manufactured by Mixpac) and expressed as a homogeneous mixture via a static mixer.

A low-viscosity impression material according to ISO 4823 was obtained, on which an applied drop of water achieved a contact angle of less than 10° after 30 seconds.

Example B8

50 parts of the paste of component II according to variant B were charged with 50 parts of the paste of component I according to variant 8 into a cartridge (manufactured by Mixpac) and expressed as a homogeneous mixture via a static mixer.

A low-viscosity impression material according to ISO 4823 was obtained, on which an applied drop of water achieved a contact angle of less than 10° within 10 seconds.

Example C7

50 parts of the paste of component II according to variant C were charged with 50 parts of the paste of component I according to variant 7 into a cartridge (manufactured by Mixpac) and expressed as a homogeneous mixture via a static mixer.

A low-viscosity impression material according to ISO 4823 was obtained, on which an applied drop of water achieved a contact angle of less than 10° after 30 seconds.

Example C8

50 parts of the paste of component II according to variant C were charged with 50 parts of the paste of component I according to variant 8 into a cartridge (manufactured by Mixpac) and expressed as a homogeneous mixture via a static mixer.

A low-viscosity impression material according to ISO 4823 was obtained, on which an applied drop of water achieved a contact angle of less than 10° within 10 seconds.

Example D7

50 parts of the paste of component II according to variant D were charged with 50 parts of the paste of component I according to variant 7 into a cartridge (manufactured by Mixpac) and expressed as a homogeneous mixture via a static mixer.

A low-viscosity impression material according to ISO 4823 was obtained, on which an applied drop of water achieved a contact angle of less than 10° within 10 seconds.

Example D8

50 parts of the paste of component II according to variant D were charged with 50 parts of the paste of component I according to variant 8 into a cartridge (manufactured by Mixpac) and expressed as a homogeneous mixture via a static mixer.

A low-viscosity impression material according to ISO 4823 was obtained, on which an applied drop of water achieved a contact angle of less than 10° within 10 seconds.

Compositions According to the Invention Comprising Surfactant 3, Surfactant 1 and Surfactant 2

Example E6

50 parts of the paste of component II according to variant E were charged with 50 parts of the paste of component I according to variant 6 into a cartridge (manufactured by Mixpac) and expressed as a homogeneous mixture via a static mixer.

A low-viscosity impression material according to ISO 4823 was obtained, on which an applied drop of water achieved a contact angle of less than 10° after 28 seconds.

Example E7

50 parts of the paste of component II according to variant E were charged with 50 parts of the paste of component I according to variant 7 into a cartridge (manufactured by Mixpac) and expressed as a homogeneous mixture via a static mixer.

A low-viscosity impression material according to ISO 4823 was obtained, on which an applied drop of water achieved a contact angle of less than 10° within 10 seconds.

Example E8

50 parts of the paste of component II according to variant E were charged with 50 parts of the paste of component I according to variant 8 into a cartridge (manufactured by Mixpac) and expressed as a homogeneous mixture via a static mixer.

A low-viscosity impression material according to ISO 4823 was obtained, on which an applied drop of water achieved a contact angle of less than 10° within 10 seconds.

Example F6

50 parts of the paste of component II according to variant F were charged with 50 parts of the paste of component I according to variant 6 into a cartridge (manufactured by Mixpac) and expressed as a homogeneous mixture via a static mixer.

A low-viscosity impression material according to ISO 4823 was obtained, on which an applied drop of water achieved a contact angle of less than 10° after 12 seconds.

Example F7

50 parts of the paste of component II according to variant F were charged with 50 parts of the paste of component I according to variant 7 into a cartridge (manufactured by Mixpac) and expressed as a homogeneous mixture via a static mixer.

A low-viscosity impression material according to ISO 4823 was obtained, on which an applied drop of water achieved a contact angle of less than 10° within 10 seconds.

Example F8

50 parts of the paste of component II according to variant F were charged with 50 parts of the paste of component I according to variant 8 into a cartridge (manufactured by Mixpac) and expressed as a homogeneous mixture via a static mixer.

A low-viscosity impression material according to ISO 4823 was obtained, on which an applied drop of water achieved a contact angle of less than 10° within 10 seconds.

Example G6

50 parts of the paste of component II according to variant G were charged with 50 parts of the paste of component I according to variant 6 into a cartridge (manufactured by Mixpac) and expressed as a homogeneous mixture via a static mixer.

A low-viscosity impression material according to ISO 4823 was obtained, on which an applied drop of water achieved a contact angle of less than 10° within 10 seconds.

Example G7

50 parts of the paste of component II according to variant G were charged with 50 parts of the paste of component I according to variant 7 into a cartridge (manufactured by Mixpac) and expressed as a homogeneous mixture via a static mixer.

A low-viscosity impression material according to ISO 4823 was obtained, on which an applied drop of water achieved a contact angle of less than 10° within 10 seconds.

Example G8

50 parts of the paste of component II according to variant G were charged with 50 parts of the paste of component I according to variant 8 into a cartridge (manufactured by Mixpac) and expressed as a homogeneous mixture via a static mixer.

A low-viscosity impression material according to ISO 4823 was obtained, on which an applied drop of water achieved a contact angle of less than 10° within 10 seconds.

Comparative Examples

Not According to the Invention

Comparative Examples Containing Only Surfactant 1

Example A1

Comparative Example with 0.25% of Surfactant 1

50 parts of the paste of component II according to variant A were charged with 50 parts of the paste of component I according to variant 1 into a cartridge (manufactured by Mixpac) and expressed as a homogeneous mixture via a static mixer.

A low-viscosity impression material according to ISO 4823 was obtained, on which an applied drop of water exhibited a contact angle of more than 90° after 30 seconds.

Example A2

Comparative Example with 0.5% of Surfactant 1

50 parts of the paste of component II according to variant A were charged with 50 parts of the paste of component I according to variant 2 into a cartridge (manufactured by Mixpac) and expressed as a homogeneous mixture via a static mixer.

A low-viscosity impression material according to ISO 4823 was obtained, on which an applied drop of water exhibited a contact angle of more than 90° after 30 seconds.

Example A3

Comparative Example with 1% of Surfactant 1

50 parts of the paste of component II according to variant A were charged with 50 parts of the paste of component I according to variant 3 into a cartridge (manufactured by Mixpac) and expressed as a homogeneous mixture via a static mixer.

A low-viscosity impression material according to ISO 4823 was obtained, on which an applied drop of water achieved a contact angle of 70° after 30 seconds.

Example B1

Comparative Example with 0.5% of Surfactant 1

50 parts of the paste of component II according to variant B were charged with 50 parts of the paste of component I according to variant 1 into a cartridge (manufactured by Mixpac) and expressed as a homogeneous mixture via a static mixer.

A low-viscosity impression material according to ISO 4823 was obtained, on which an applied drop of water exhibited a contact angle of more than 90° after 30 seconds.

Example B2

Comparative Example with 0.75% of Surfactant 1

50 parts of the paste of component II according to variant B were charged with 50 parts of the paste of component I according to variant 2 into a cartridge (manufactured by Mixpac) and expressed as a homogeneous mixture via a static mixer.

A low-viscosity impression material according to ISO 4823 was obtained, on which an applied drop of water exhibited a contact angle of more than 90° after 30 seconds.

Example B3

Comparative Example with 1.25% of Surfactant 1

50 parts of the paste of component II according to variant B were charged with 50 parts of the paste of component I according to variant 3 into a cartridge (manufactured by Mixpac) and expressed as a homogeneous mixture via a static mixer.

A low-viscosity impression material according to ISO 4823 was obtained, on which an applied drop of water exhibited a contact angle of 58° after 30 seconds, a contact angle of less than 10° was not achieved.

Example C1

Comparative Example with 0.75% of Surfactant 1

50 parts of the paste of component II according to variant C were charged with 50 parts of the paste of component I according to variant 1 into a cartridge (manufactured by Mixpac) and expressed as a homogeneous mixture via a static mixer.

A low-viscosity impression material according to ISO 4823 was obtained, on which an applied drop of water exhibited a contact angle of more than 90° after 30 seconds.

Example C2

Comparative Example with 1% of Surfactant 1

50 parts of the paste of component II according to variant C were charged with 50 parts of the paste of component I according to variant 2 into a cartridge (manufactured by Mixpac) and expressed as a homogeneous mixture via a static mixer.

A low-viscosity impression material according to ISO 4823 was obtained, on which an applied drop of water exhibited a contact angle of 64° after 30 seconds, a contact angle of less than 10° was not achieved.

Example C3

Comparative Example with 1.5% of Surfactant 1

50 parts of the paste of component II according to variant C were charged with 50 parts of the paste of component I according to variant 3 into a cartridge (manufactured by Mixpac) and expressed as a homogeneous mixture via a static mixer.

A low-viscosity impression material according to ISO 4823 was obtained, on which an applied drop of water exhibited a contact angle of 53° after 30 seconds, a contact angle of less than 10° was not achieved.

Example D1

Comparative Example with 1.25% of Surfactant 1

50 parts of the paste of component II according to variant D were charged with 50 parts of the paste of component I according to variant 1 into a cartridge (manufactured by Mixpac) and expressed as a homogeneous mixture via a static mixer.

A low-viscosity impression material according to ISO 4823 was obtained, on which an applied drop of water exhibited a contact angle of 56° after 30 seconds, a contact angle of less than 10° was not achieved.

Example D2

Comparative Example with 1.5% of Surfactant 1

50 parts of the paste of component II according to variant D were charged with 50 parts of the paste of component I according to variant 2 into a cartridge (manufactured by Mixpac) and expressed as a homogeneous mixture via a static mixer.

A low-viscosity impression material according to ISO 4823 was obtained, on which an applied drop of water exhibited a contact angle of 52° after 30 seconds, a contact angle of less than 10° was not achieved.

Example D3

Comparative Example with 2% of Surfactant 1

50 parts of the paste of component II according to variant D were charged with 50 parts of the paste of component I according to variant 3 into a cartridge (manufactured by Mixpac) and expressed as a homogeneous mixture via a static mixer.

A low-viscosity impression material according to ISO 4823 was obtained, on which an applied drop of water exhibited a contact angle of 50° after 30 seconds, a contact angle of less than 10° was not achieved.

Comparative examples containing only surfactant 3

Example A4

Comparative Example with 0.5% of Surfactant 3

50 parts of the paste of component II according to variant A were charged with 50 parts of the paste of component I according to variant 4 into a cartridge (manufactured by Mixpac) and expressed as a homogeneous mixture via a static mixer.

A low-viscosity impression material according to ISO 4823 was obtained, on which an applied drop of water achieved a contact angle of 64° after 30 seconds.

Example A5

Comparative Example with 1% of Surfactant 3

50 parts of the paste of component II according to variant A were charged with 50 parts of the paste of component I according to variant 5 into a cartridge (manufactured by Mixpac) and expressed as a homogeneous mixture via a static mixer.

A low-viscosity impression material according to ISO 4823 was obtained, on which an applied drop of water achieved a contact angle of 55° after 30 seconds.

Example E4

Comparative Example with 1% of Surfactant 3

50 parts of the paste of component II according to variant E were charged with 50 parts of the paste of component 1 according to variant 4 into a cartridge (manufactured by Mixpac) and expressed as a homogeneous mixture via a static mixer.

A low-viscosity impression material according to ISO 4823 was obtained, on which an applied drop of water achieved a contact angle of 53° after 30 seconds.

Example E5

Comparative Example with 1.5% of Surfactant 3

50 parts of the paste of component II according to variant E were charged with 50 parts of the paste of component 1 according to variant 5 into a cartridge (manufactured by Mixpac) and expressed as a homogeneous mixture via a static mixer.

A low-viscosity impression material according to ISO 4823 was obtained, on which an applied drop of water achieved a contact angle of 30° after 30 seconds.

Example F4

Comparative Example with 1.5% of Surfactant 3

50 parts of the paste of component II according to variant F were charged with 50 parts of the paste of component 1 according to variant 4 into a cartridge (manufactured by Mixpac) and expressed as a homogeneous mixture via a static mixer.

A low-viscosity impression material according to ISO 4823 was obtained, on which an applied drop of water achieved a contact angle of 32° after 30 seconds.

Example F5

Comparative Example with 2% of Surfactant 3

50 parts of the paste of component II according to variant F were charged with 50 parts of the paste of component 1 according to variant 5 into a cartridge (manufactured by Mixpac) and expressed as a homogeneous mixture via a static mixer.

A low-viscosity impression material according to ISO 4823 was obtained, on which an applied drop of water achieved a contact angle of 19° after 30 seconds.

Example G4

Comparative Example with 3% of Surfactant 3

50 parts of the paste of component II according to variant G were charged with 50 parts of the paste of component 1 according to variant 4 into a cartridge (manufactured by Mixpac) and expressed as a homogeneous mixture via a static mixer.

A low-viscosity impression material according to ISO 4823 was obtained, on which an applied drop of water achieved a contact angle of 17° after 30 seconds.

Example G5

Comparative Example with 3.5% of Surfactant 3

50 parts of the paste of component II according to variant G were charged with 50 parts of the paste of component 1 according to variant 5 into a cartridge (manufactured by Mixpac) and expressed as a homogeneous mixture via a static mixer.

A low-viscosity impression material according to ISO 4823 was obtained, on which an applied drop of water achieved a contact angle of 15° after 30 seconds.

Comparative Examples Containing Surfactant 3 and Surfactant 1

Example B4

Comparative Example with 0.5% of Surfactant 3 and 0.35% of Surfactant 1

50 parts of the paste of component II according to variant B were charged with 50 parts of the paste of component 1 according to variant 4 into a cartridge (manufactured by Mixpac) and expressed as a homogeneous mixture via a static mixer.

A low-viscosity impression material according to ISO 4823 was obtained, on which an applied drop of water exhibited a contact angle of 62° after 30 seconds; a contact angle of less than 10° was not achieved.

Example B5

Comparative Example with 1% of surfactant 3 and 0.25% of surfactant 1

50 parts of the paste of component II according to variant B were charged with 50 parts of the paste of component 1 according to variant 5 into a cartridge (manufactured by Mixpac) and expressed as a homogeneous mixture via a static mixer.

A low-viscosity impression material according to ISO 4823 was obtained, on which an applied drop of water exhibited a contact angle of 45° after 30 seconds; a contact angle of less than 10° was not achieved.

Example C4

Comparative Example with 0.5% of Surfactant 3 and 0.5% of Surfactant 1

50 parts of the paste of component II according to variant C were charged with 50 parts of the paste of component 1 according to variant 4 into a cartridge (manufactured by Mixpac) and expressed as a homogeneous mixture via a static mixer.

A low-viscosity impression material according to ISO 4823 was obtained, on which an applied drop of water exhibited a contact angle of 47° after 30 seconds; a contact angle of less than 10° was not achieved.

Example C5

Comparative Example with 1% of surfactant 3 and 0.5% of surfactant 1

50 parts of the paste of component II according to variant C were charged with 50 parts of the paste of component 1 according to variant 5 into a cartridge (manufactured by Mixpac) and expressed as a homogeneous mixture via a static mixer.

A low-viscosity impression material according to ISO 4823 was obtained, on which an applied drop of water exhibited a contact angle of 40° after 30 seconds; a contact angle of less than 10° was not achieved.

Example D4

Comparative Example with 0.5% of Surfactant 3 and 1% of Surfactant 1

50 parts of the paste of component II according to variant D were charged with 50 parts of the paste of component I according to variant 4 into a cartridge (manufactured by Mixpac) and expressed as a homogeneous mixture via a static mixer.

A low-viscosity impression material according to ISO 4823 was obtained, on which an applied drop of water exhibited a contact angle of 31° after 30 seconds; a contact angle of less than 10° was not achieved.

Example D5

Comparative Example with 1% of Surfactant 3 and 1% of Surfactant 1

50 parts of the paste of component II according to variant D were charged with 50 parts of the paste of component I according to variant 4 into a cartridge (manufactured by Mixpac) and expressed as a homogeneous mixture via a static mixer.

A low-viscosity impression material according to ISO 4823 was obtained, on which an applied drop of water exhibited a contact angle of 22° after 30 seconds; a contact angle of less than 10° was not achieved.

Example E1

50 parts of the paste of component II according to variant E were charged with 50 parts of the paste of component I according to variant 1 into a cartridge (manufactured by Mixpac) and expressed as a homogeneous mixture via a static mixer.

A low-viscosity impression material according to ISO 4823 was obtained, on which an applied drop of water exhibited a contact angle of 67° after 30 seconds; a contact angle of less than 10° was not achieved.

Example E2

50 parts of the paste of component II according to variant E were charged with 50 parts of the paste of component I according to variant 2 into a cartridge (manufactured by Mixpac) and expressed as a homogeneous mixture via a static mixer.

A low-viscosity impression material according to ISO 4823 was obtained, on which an applied drop of water exhibited a contact angle of 61° after 30 seconds; a contact angle of less than 10° was not achieved.

Example E3

50 parts of the paste of component II according to variant E were charged with 50 parts of the paste of component I according to variant 3 into a cartridge (manufactured by Mixpac) and expressed as a homogeneous mixture via a static mixer.

A low-viscosity impression material according to ISO 4823 was obtained, on which an applied drop of water exhibited a contact angle of 39° after 30 seconds; a contact angle of less than 10° was not achieved.

Example F1

50 parts of the paste of component II according to variant F were charged with 50 parts of the paste of component I according to variant 1 into a cartridge (manufactured by Mixpac) and expressed as a homogeneous mixture via a static mixer.

A low-viscosity impression material according to ISO 4823 was obtained, on which an applied drop of water exhibited a contact angle of 47° after 30 seconds; a contact angle of less than 10° was not achieved.

Example F2

50 parts of the paste of component II according to variant F were charged with 50 parts of the paste of component I according to variant 2 into a cartridge (manufactured by Mixpac) and expressed as a homogeneous mixture via a static mixer.

A low-viscosity impression material according to ISO 4823 was obtained, on which an applied drop of water exhibited a contact angle of 40° after 30 seconds; a contact angle of less than 10° was not achieved.

Example F3

50 parts of the paste of component II according to variant F were charged with 50 parts of the paste of component I according to variant 3 into a cartridge (manufactured by Mixpac) and expressed as a homogeneous mixture via a static mixer.

A low-viscosity impression material according to ISO 4823 was obtained, on which an applied drop of water exhibited a contact angle of 39° after 30 seconds; a contact angle of less than 10° was not achieved.

Example G1

50 parts of the paste of component II according to variant G were charged with 50 parts of the paste of component I according to variant 1 into a cartridge (manufactured by Mixpac) and expressed as a homogeneous mixture via a static mixer.

A low-viscosity impression material according to ISO 4823 was obtained, on which an applied drop of water exhibited a contact angle of 18° after 30 seconds; a contact angle of less than 10° was not achieved.

Example G2

50 parts of the paste of component II according to variant G were charged with 50 parts of the paste of component I according to variant 2 into a cartridge (manufactured by Mixpac) and expressed as a homogeneous mixture via a static mixer.

A low-viscosity impression material according to ISO 4823 was obtained, on which an applied drop of water exhibited a contact angle of 20° after 30 seconds; a contact angle of less than 10° was not achieved.

Example G3

50 parts of the paste of component II according to variant G were charged with 50 parts of the paste of component I according to variant 3 into a cartridge (manufactured by Mixpac) and expressed as a homogeneous mixture via a static mixer.

A low-viscosity impression material according to ISO 4823 was obtained, on which an applied drop of water exhibited a contact angle of 21° after 30 seconds; a contact angle of less than 10° was not achieved.

Comparative Examples Containing Surfactant 1 and Surfactant 2

Example A6

50 parts of the paste of component II according to variant A were charged with 50 parts of the paste of component I according to variant 6 into a cartridge (manufactured by Mixpac) and expressed as a homogeneous mixture via a static mixer.

A low-viscosity impression material according to ISO 4823 was obtained, on which an applied drop of water exhibited a contact angle of 85° after 30 seconds.

Example A7

50 parts of the paste of component II according to variant A were charged with 50 parts of the paste of component I according to variant 7 into a cartridge (manufactured by Mixpac) and expressed as a homogeneous mixture via a static mixer.

A low-viscosity impression material according to ISO 4823 was obtained, on which an applied drop of water exhibited a contact angle of 20° after 30 seconds; a contact angle of less than 10° was achieved after 44 seconds.

Example B6

50 parts of the paste of component II according to variant B were charged with 50 parts of the paste of component I according to variant 6 into a cartridge (manufactured by Mixpac) and expressed as a homogeneous mixture via a static mixer.

A low-viscosity impression material according to ISO 4823 was obtained, on which an applied drop of water exhibited a contact angle of 45° after 30 seconds; a contact angle of less than 10° was achieved after 80 seconds.

Example C6

50 parts of the paste of component II according to variant C were charged with 50 parts of the paste of component I according to variant 6 into a cartridge (manufactured by Mixpac) and expressed as a homogeneous mixture via a static mixer.

A low-viscosity impression material according to ISO 4823 was obtained, on which an applied drop of water exhibited a contact angle of 25° after 30 seconds; a contact angle of less than 10° was achieved after 65 seconds.

Example D6

50 parts of the paste of component II according to variant D were charged with 50 parts of the paste of component I according to variant 6 into a cartridge (manufactured by Mixpac) and expressed as a homogeneous mixture via a static mixer.

A low-viscosity impression material according to ISO 4823 was obtained, on which an applied drop of water exhibited a contact angle of 13° after 30 seconds;

a contact angle of less than 10° was achieved after 39 seconds.

TABLE 1

Contact angle after 30 seconds

| Component I | Component II | | | | | | |
|---|---|---|---|---|---|---|---|
| | A | B | C | D | E | F | G |
| 1 | >90° | >90° | >90° | 56° | 67° | 47° | 18° |
| 2 | >90° | >90° | 64° | 52° | 61° | 40° | 20° |
| 3 | 70° | 58° | 53° | 50° | 39° | 39° | 21° |
| 4 | 64° | 62° | 47° | 31° | 53° | 32° | 17° |
| 5 | 55° | 45° | 40° | 22° | 30° | 41° | 15° |
| 6 | 85° | 45° | 25° | 13° | <10° | <10° | <10° |
| 7 | 20° | <10° | <10° | <10° | <10° | <10° | <10° |
| 8 | <10° | <10° | <10° | <10° | <10° | <10° | <10° |

TABLE 2

| | Time taken to achieve a contact angle of <10° | | | | | | |
|---|---|---|---|---|---|---|---|
| | Component II | | | | | | |
| Component I | A | B | C | D | E | F | G |
| 1 | — | — | — | — | — | — | — |
| 2 | — | — | — | — | — | — | — |
| 3 | — | — | — | — | — | — | — |
| 4 | — | — | — | — | — | — | — |
| 5 | — | — | — | — | — | — | — |
| 6 | — | 80 s | 65 s | 39 s | 28s | 12 s | <10 s |
| 7 | 44 s | 30 s | 30 s | <10 s | <10 s | <10 s | <10 s |
| 8 | 21 s | <10 s | <10 s | <10 s | <10 s | <10 s | <10 s |

The invention claimed is:

1. A curable, single- or multi-component composition for dental impression, comprising:
a curable base composition
and
a surfactant system comprising
0.5 to 3% by weight of a first surfactant, which is one or more compounds of formula

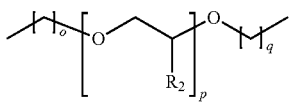

wherein
o is an integer from 5 to 22,
p is an integer from 2 to 20,
q is an integer from 0 to 5, and
$R_2$ is independently hydrogen or methyl for each repeat unit,
0.5 to 3% by weight of a second surfactant, selected from the group of non-ionic fluorosurfactants,
0 to 3% by weight of a third surfactant, selected from the group of silicone surfactants,
wherein the total quantity of first, second and third surfactant is within the range of from 1.5% by weight to 6% by weight, provided that
the mass ratio of the first surfactant to the second surfactant is 1.4 or less when the content of the third surfactant is within the range of from 0 to less than 0.5% by weight and the total quantity of first and second surfactant is 2% by weight or less,
all the percentages by weight being based on the total mass of the composition.

2. The curable composition as claimed in claim 1, comprising
a curable base composition
and
a surfactant system comprising
the first surfactant
a second surfactant selected from the group of non-ionic fluorosurfactants,
optionally a third surfactant selected from the group of silicone surfactants,
provided that the surfactant system contains
0.75 to 3% by weight of the second surfactant,
0 to less than 0.5% by weight of the third surfactant,
or the surfactant system contains
0.5 to 2.5% by weight of the first surfactant,
0.5 to 2.5% by weight of the second surfactant
0.5 to 2.5% by weight of the third surfactant.

3. The curable composition as claimed in claim 1, wherein the composition is a multi-component, comprising a first component and it second component, the constituents of which are adapted to one another such that curing is initiated by mixing the first and second components as well as optionally present further components.

4. The curable composition as claimed in claim 1, wherein the curable base composition is selected from the group of
organopolysiloxanes crosslinking by an addition reaction,
organopolysiloxanes crosslinking by a condensation reaction,
polyethers containing aziridino radicals crosslinking by an addition reaction,
polyethers containing alkenyl radicals crosslinking by an addition reaction,
polyethers containing alkoxysilyl radicals crosslinking by a condensation reaction.

5. The curable composition as claimed in claim 4, wherein the curable base composition is an organopolysiloxane crosslinking by an addition reaction, comprising
an organopolysiloxane with at least two ethylenically unsaturated groups
and
an organohydrogen polysiloxane.

6. The curable composition as claimed in claim 5, wherein the composition is a multi-component system, comprising
a first component comprising organopolysiloxane with at least two ethylenically unsaturated groups and a hydrosilylation catalyst,
and
a second component comprising the organohydrogen polysiloxane and optionally organopolysiloxane with at least two ethylenically unsaturated groups.

7. The curable composition as claimed in claim 6, wherein the first surfactant and the second surfactant, and optionally further surfactants, are contained in the first and/or second component.

8. The curable composition as claimed in claim 1, further comprising one or more fillers and optionally further additives.

9. The curable composition as claimed in claim 1, comprising
a curable base composition and
a surfactant system comprising
0.75 to 3% by weight of the first surfactant
0.75 to 3% by weight of a second surfactant, selected from the group of non-ionic fluorosurfactants,
0 to less than 0.5% by weight of a third surfactant, selected from the group of silicone surfactants,
wherein the total quantity of first, second and third surfactant is within the range of from 2 to 6% by weight,
the mass ratio of the first surfactant to the second surfactant is 1.4 or less when the content of the third surfactant is within the range of from 0 to less than 0.5% by weight and the total quantity of first and second surfactants is 2% by weight,
all the percentages by weight being based on the total mass of the composition.

10. The curable composition as claimed in claim 1, comprising
a curable base composition and
a surfactant system comprising
0.5 to 2.5% by weight of the first surfactant
0.5 to 2.5% by weight of a second surfactant, selected from the group of non-ionic fluorosurfactants,
0.5 to 2.5% by weight of a third surfactant, selected from the group of silicone surfactants, wherein the total quantity of first, second and third surfactant is within the range of from 1.75% by weight to 6% by weight, and, when the total quantity of first, second and third surfactant amounts to 2% by weight or less, the quantity of the second surfactant amounts to at least 0.75% by weight, all the percentages by weight being based on the total mass of the composition.

11. The curable composition as claimed in claim 1, Wherein the second surfactant is a compound of formula:

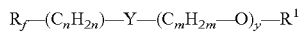

wherein $R_f$ is a radical of the formula $C_xF_{2x+1}$, x is an integer from 1 to 30, n is an integer from 0 to 30, Y is —O— or —CO—O—, m is an integer from 2 to 6, where m can assume different values within a molecule in the scope of the given definition, y is an integer from 1 to 60, and $R_1$ represents hydrogen or a monovalent organic radical.

12. The curable composition as claimed in claim 11, wherein:

(1) x is an integer from 2 to 18, (2) n is an integer from 1 to 3, (3) is —O—, (4) in is an integer from 2 or 3, where in can assume different values within a molecule in the scope of the given definition, (5) y is an integer from 1 to 25, (6) $R_1$ represents hydrogen, $C_1$-$C_6$ alkyl or phenyl or a combination of (1)-(6).

13. The curable composition as claimed in claim 11, wherein:

m is 2, where m can assume different values within a molecule in the scope of the given definition and/or $R_1$ represents hydrogen or an alkyl radical.

14. A method of obtaining a denial impression comprising: producing a curable composition as claimed in claim 1; and contacting said curable composition with a dental feature to form an impression of said dental feature.

15. The method of claim 14, further comprising, curing the curable composition.

16. A process for the preparation of a composition as claimed in claim 1, comprising the steps:

preparation of a curable base composition preparation of a surfactant system comprising 0.5 to 3% by weight of the first surfactant 0.5 to 3% by weight of a second surfactant, selected from the group of non-ionic fluorosurfactants, 0 to 3% by weight of a third surfactant, selected from the group of silicone surfactants, wherein the total quantity of first, second and third surfactant is within the range of from 1.5% by weight to 6% by weight, provided that the mass ratio of the first surfactant to the second surfactant is 1.4 or less when the content of the third surfactant is within the range of from 0 to less than 0.5% by weight and the total quantity of first and second surfactant is 2% by weight or less, all the percentages by weight being based on the total mass of the composition.

17. The curable composition according to claim 2, wherein the surfactant system comprises:

0.5 to 2.5% by weight of the first surfactant;

0.75 to 2.5% by weight of the second surfactant; and 0.5 to 2.5% by weight of the third surfactant.

18. The curable composition according to claim 1, wherein the third surfactant is selected from the group of silicone surfactants, excluding non-ionic, silicon-containing surfactants with at least one (poly)alkylene oxide radical having a molar mass of less than 6000 g/mol.

* * * * *

UNITED STATES PATENT AND TRADEMARK OFFICE
CERTIFICATE OF CORRECTION

PATENT NO. : 8,916,623 B2
APPLICATION NO. : 13/105619
DATED : December 23, 2014
INVENTOR(S) : Norman Hendrik Riedel and Mandred Thomas Plaumann It is certified that error appears in the above-identified patent and that said Letters Patent is hereby corrected as shown below:

In the claims

In Column 26, line 3 of Claim 3 reads "component and it second component, the constituents of"

but should read "component and a second component, the constituents of"

In Column 27, line 12 of Claim 11 reads "$R_f\text{—}(C_nH_{2n})\text{—}Y\text{—}(C_mH_{2m}\text{—}O)_y\text{—}R^1$"

but should read "$R_f\text{—}(C_nH_{2n})\text{—}Y\text{—}(C_mH_{2m}\text{—}O)_y\text{—}R_1$"

In Column 27, line 27 of Claim 12 reads "is —O—"

but should read "y is —O—"

In Column 27, line 28 of Claim 12 reads "in is an integer from 2 or 3, where in can assume"

but should read "m is an integer from 2 or 3, where m can assume"

Signed and Sealed this
Sixth Day of October, 2015

Michelle K. Lee
*Director of the United States Patent and Trademark Office*